United States Patent [19]
Bredeweg

[11] 3,939,212
[45] Feb. 17, 1976

[54] CHLORINATED AND BROMINATED CARBOCYCLIC DIETHERS

[75] Inventor: Corwin J. Bredeweg, Midland, Mich.

[73] Assignee: The Dow Chemical Company, Midland, Mich.

[22] Filed: Dec. 4, 1972

[21] Appl. No.: 311,456

[52] U.S. Cl............................. 260/611 R; 260/611 A
[51] Int. Cl.²................... C07C 43/18; C07C 43/28
[58] Field of Search ................................. 260/611 R

[56] References Cited
UNITED STATES PATENTS 2,644,012  6/1953  Korman et al. ................. 260/611 R
2,645,666  7/1953  Hogg .............................. 260/611 R

FOREIGN PATENTS OR APPLICATIONS 204,687  5/1939  Switzerland..................... 260/611 R

*Primary Examiner*—Donald G. Daus
*Assistant Examiner*—D. B. Springer
*Attorney, Agent, or Firm*—David H. Fifield

[57] ABSTRACT

The invention consists of the compounds of the formula

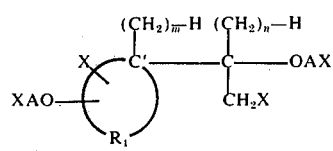

(hereinafter DE), wherein X is chlorine or bromine, A is a vicinal alkylene of from 2 to about 8 carbon atoms which may bear a phenyl, hydroxy, chlorine or bromine substituent and $R_1$ is an alkylene of from 4 to about 7 carbon atoms, two terminal carbon atoms of which are joined to C' to form a carbocyclic group upon which X- and XAO- are vicinally substituted and m and n are independently 0 or 1.

These compounds are prepared by reacting the halogen XX with a mixture of the appropriate vinyl $R_1$ cycloalkene (hereinafter $VCR_1$), and the epoxide AO. Such compounds are useful as solvents and as reactants in the production of cycloaliphatic polythiols which are useful in curing polyepoxide resins.

11 Claims, No Drawings

CHLORINATED AND BROMINATED CARBOCYCLIC DIETHERS

BACKGROUND OF THE INVENTION

1. Field of the Invention:

The novel and useful compounds disclosed belong to the subclass of chlorinated and brominated diethers where one ether linkage is directly attached to a carbon atom in a lower carbocyclic ring and the other is attached to a chlorethyl substituent on the ring. The process for making these compounds may be generally described as the addition of a chlorine or a bromine atom and an ether linkage on each of two points of unsaturation in a vinyl cyclomonoalkene.

2. Description of the Prior Art:

Several compounds of this invention are disclosed in the application of Hickner and Goss, Ser. No. 245,185, filed Apr. 18, 1972. Related chlorinated and brominated acyclic ethers are disclosed in my U.S. Application, Serial No. 306,916, filed November 15, 1972. Prior art cited therein teaches the preparation of ethers by the reaction of chlorine, ethylene oxide and cyclohexene: Dinulescu et al., *Chemistry and Industry*, (London 1964): 840–841.

SUMMARY OF THE INVENTION

The invention consists of compounds having the formula

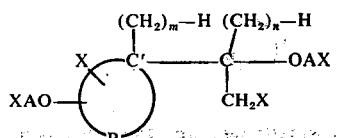

(hereinafter DE), wherein each X is independently chlorine or bromine, A is a vicinal alkylene of from 2 to about 8 carbon atoms which may bear a phenyl, hydroxy, chlorine or bromine substituent and $R_1$ is an alkylene of from 4 to about 7 atoms, two terminal carbon atoms of which are joined to $C'$ to form a carbocyclic group upon which X- and XAO- are vicinally substituted and m and n are independently 0 or 1. The compounds are useful as solvents and as reactants in the production of cycloaliphatic polythiols useful in curing polyepoxide resins.

DETAILED DESCRIPTION OF THE INVENTION

The DE compounds are prepared by mixing an excess amount of an AO, preferably ethylene oxide, propylene oxide, butylene oxide, styrene oxide, epichlorohydrin or glycidol, with a vinylcycloalkene, $VCR_1$, of from 7 to about 10 carbon atoms, preferably 4-vinylcyclohexene, suitably in the molar ratio of AO to $VCR_1$ of about 4 to 1 and reacting the mixture by contacting with a sufficient amount of bromine chloride, chlorine or bromine, suitably with the halogen XX and $VCR_1$ in ratios of about 2 to 1.

The $VCR_1$ employed may be substantially any vinylcycloalkene of from 7 to about 10 carbon atoms wherein the cycloalkene ring contains only one olefinic linkage. Carbon atoms of the $VCR_1$ may bear methyl or ethyl substituents. Preferably, the $VCR_1$ has about 7 or 8 carbon atoms and $C'$ is found at the 4 position in a cyclohexene or cyclopentene ring.

The preparation of the DE compounds is conveniently carried out at atmospheric pressure and at a temperature of about 0° to 100°C. The temperature may be lowered as long as the reactants do not solidify. The temperature may be increased to at least about 200°C. if the operation is carried out in an enclosed pressurized vessel at a sufficient pressure to keep the nonhalogen reactants from boiling. The reaction with chlorine or bromine is instantaneous. (Caution: The halogens should preferably be added to a mixture of the other two reactants since a reaction of the halogen with the epoxide alone may be quite violent.)

The reaction mixture is subsequently distilled, suitably at reduced pressures, to remove excess epoxide and other low-boiling volatiles. The invention compounds may be used as solvents and as reactants in the production of cycloaliphatic polythiols which are useful in curing polyepoxide resins.

The reaction product is composed of a cogeneric mixture of various isomeric compounds, depending on the mode of addition of the reactants to the olefinic double bond in the $VCR_1$ ring and on the position of the breaking of one of the C-O bonds in the AO material for AO's other than ethylene oxide. Since the mixture of isomers has similar properties and may be put to the same uses as the single compounds, the mixed product may be employed in the solvent and reactant uses described above and its separation is consequently unnecessary.

DESCRIPTION OF SPECIFIC EMBODIMENTS OF THE INVENTION

Each of the following examples of the invention is prepared by carrying out the above-described process at about 0° to 50°C., under atmospheric pressure employing the corresponding AO, $VCR_1$, and halogen reactants. The halogen is added to the AO-$VCR_1$ mixture until the mixture begins to turn slightly yellow in color.

The preferred molar ratio of 4:1, AO:$VCR_1$, is employed to avoid large amounts of undesired excessively chlorinated or brominated by-products. Distillation at reduced pressure is used to remove excess AO and lower-boiling by-products. The reaction product usually contains small amounts of telomers of the basic DE invention wherein the AO groups are repeated one or more times. The crude products are useful in the same solvent and polythiol production reactant applications as the pure compounds, thereby obviating the need for separation, which could suitably be performed by fractional distillation of the telomers.

EXAMPLE 1

Chlorine gas, in the amount of 240 g. (3.4 m.), was added to a stirred solution of 162 g. (1.5 m.) of 4-vinylcyclohexene and 264 g. (6 m.) of ethylene oxide through a sparger tube at a rate of about 1 mole of chlorine per hour. A reaction temperature of from 5°–20°C. was maintained by cooling the mixture in an ice bath while the addition of chlorine proceeded. The mixture was subsequently distilled at 0.2 mm. pressure to remove excess ethylene oxide and other low-boiling volatiles. About 490 g. of product was recovered as residue when the pot temperature reached 100°C. at 0.2 mm. pressure. Gravimetric analysis indicated the presence of chlorine at 43.6% of the product by weight. Theoretical calculations of the chlorine content of isomers of the compound

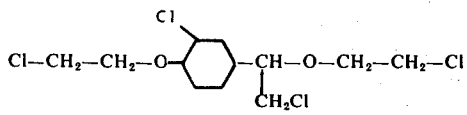

indicated that chlorine would be 42.0% by weight. The difference is believed due to the presence of chlorinated by-products.

EXAMPLE 2

To a stirred solution of 162 g. (1.5 m.) of 4-vinylcyclohexene and 348 g. (6 m.) of propylene oxide 247 g. (3.5 m.) of chlorine gas was added by bubbling the chlorine through the solution. The chlorine was added at the rate of about 1 mole per hour and the reaction mixture was cooled in an ice bath to maintain a reaction temperature of from about 3°–20°C. The mixture was subsequently distilled at reduced pressures to remove excess propylene oxide and low-boiling volatiles. After those materials were removed, about 520 g. of residual product was recovered. Gravimetric analysis of the product indicated 39.7% chlorine content by weight while theoretical calculations predicted 38.8% chlorine content by weight, based upon the compound

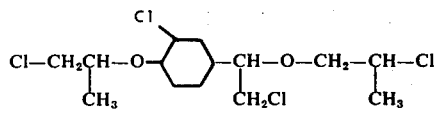

and its isomers.

EXAMPLE 3

To a stirred solution of 324 g. (3 m.) of 4-vinylcyclohexene and 1106 g. (12m.) of epichlorohydrin, 481 g. (6.8 m.) of chlorine gas was added by bubbling the chlorine through the solution. Chlorine was added at the rate of about 1 mole per hour while a reaction temperature of from about 5°–25°C. was maintained by cooling the reaction mixture in an ice bath. Fractional distillation removed epichlorohydrin and low-boiling volatiles and about 1370 g. of product-residue was recovered.

In addition to the above-described specific embodiments of the invention, other $VCR_1$ and epoxides may be combined and reacted with the XX halogen as described above. Some examples of other suitable reactant combinations which may be used to produce compounds of the invention are listed in the following table.

TABLE OF EXAMPLES OF THE INVENTION-PRODUCTS OF THE FOLLOWING REACTANTS

| Vinylcyclo-olefin ($VCR_1$) | Epoxide (AO) | Halogen (XX) |
|---|---|---|
| 3-Vinylcyclohexene | Ethylene oxide | $Cl_2$ |
| 4-Vinylcyclopentene | 1,2-Butylene oxide | BrCl |
| 3-Vinylcyclopentene | 2,3-Butylene oxide | $Br_2$ |
| 5-Vinylcycloheptene | Epichlorohydrin | $Br_2$ |
| 4-Vinylcycloheptene | Epibromohydrin | BrCl |
| 3-Vinylcycloheptene | Glycidol | $Cl_2$ |
| 6-Methyl-4-vinylcyclohexene | Propylene oxide | $Br_2$ |
| 4-Methyl-4-vinylcyclohexene | Styrene oxide | $Cl_2$ |
| 1,4-Dimethyl-4-vinylcyclohexene | 1,2-Butylene oxide | BrCl |
| 3,3-Dimethyl-4-vinylcyclohexene | Propylene oxide | BrCl |
| 5-Ethyl-4-vinylcyclopentene | Epibromohydrin | $Br_2$ |
| 1-Methyl-4-vinylcyclopentene | Ethylene oxide | $Cl_2$ |
| 3-Methyl-4-vinylcyclopentene | Styrene oxide | BrCl |
| 4-Isopropenylcyclohexene | Epichlorohydrin | $Cl_2$ |

I claim:

1. A compound represented by the formula

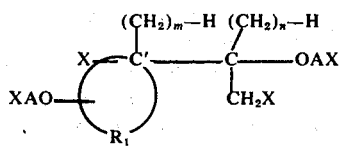

wherein each X is independently chlorine or bromine, A is a vicinal alkylene of from 2 to about 8 carbon atoms, $R_1$ is an alkylene of from 4 to 7 carbon atoms, two terminal carbon atoms of which are joined to C' to form a carbocyclic ring upon which X- and XAO- are vicinally substituted and m and n are independently zero or 1, provided that when A has the formula

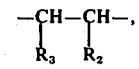

one of $R_2$ and $R_3$ is hydrogen and the other is hydrogen or an alkyl, monohydroxyalkyl, monochloroalkyl or monobromoalkyl group of from 1 to 6 carbon atoms.

2. A compound of claim 1 wherein each A has the formula

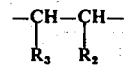

where one of $R_2$ and $R_3$ is hydrogen and the other is hydrogen, phenyl or an alkyl group of from 1 to 6 carbon atoms, which alkyl may bear a hydroxy, chlorine or bromine substituent.

3. A compound of claim 2 wherein each X is bromine.

4. A compound of claim 2 wherein each X is chlorine.

5. A compound of claim 4 wherein one of $R_2$ and $R_3$ is hydrogen and the other is hydrogen, methyl or ethyl.

6. A compound of claim 2 wherein $R_1$ consists of a 5-carbon unbranched chain and the vicinally substituted members of $R_1$ are the second and third carbon atoms from C' in the carbocyclic ring.

7. A compound of claim 6 wherein one of $R_2$ and $R_3$ is hydrogen and the other is hydrogen or an alkyl group of from 1 to 6 carbon atoms and m and n are both zero.

8. A compound of claim 6 wherein X is chlorine.

9. A compound of claim 8 wherein one of $R_2$ and $R_3$ is hydrogen and the other is hydrogen, methyl or ethyl and m and n are both zero.

10. A compound of Claim 9 represented by one of the formulas:

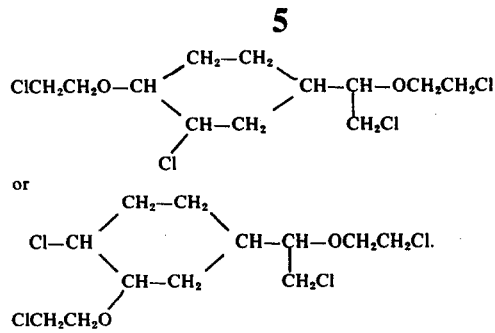
or
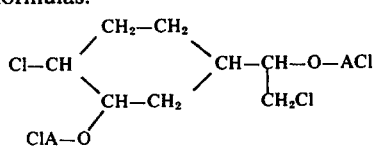
11. A compound of claim 9 represented by one of the formulas:
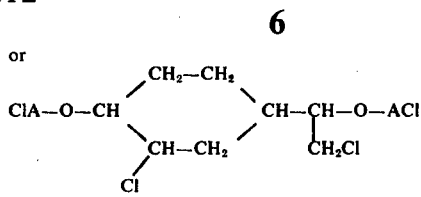
wherein -ACl is independently, each occurrence,
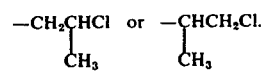
* * * * *

UNITED STATES PATENT AND TRADEMARK OFFICE
CERTIFICATE OF CORRECTION

PATENT NO. : 3,939,212
DATED : February 17, 1976
INVENTOR(S) : Corwin J. Bredeweg It is certified that error appears in the above-identified patent and that said Letters Patent are hereby corrected as shown below:

Column 4, line 32, insert --and-- after the formula;

Column 4, line 36, delete "and" in the second appearance;

Column 4, line 47, delete ", phenyl".

Signed and Sealed this

Thirty-first Day of August 1976

[SEAL]

Attest:

RUTH C. MASON
Attesting Officer

C. MARSHALL DANN
Commissioner of Patents and Trademarks